US006355430B1

(12) United States Patent
Shyjan et al.

(10) Patent No.: US 6,355,430 B1
(45) Date of Patent: Mar. 12, 2002

(54) DIAGNOSTIC AND SCREENING METHODS EMPLOYING KIAA0101

(75) Inventors: Andrew W. Shyjan, San Carlos, CA (US); Jennifer Richardson, Boston; John Vassiliadis, Marlborough, both of MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 09/470,614

(22) Filed: Dec. 22, 1999

Related U.S. Application Data

(60) Provisional application No. 60/113,581, filed on Dec. 24, 1998, now abandoned.

(51) Int. Cl.[7] .................................................. C12Q 1/68

(52) U.S. Cl. ..................... 435/6; 536/24.31; 536/24.33; 536/23.5; 530/350

(58) Field of Search ...................... 435/6, 7.1; 530/350; 536/23.1, 23.5

(56) References Cited

U.S. PATENT DOCUMENTS 6,020,135 A * 2/2000 Levine et al .................. 435/6
6,171,798 B1 * 1/2001 Levine et al. .................. 435/6

FOREIGN PATENT DOCUMENTS

WO WO00/18961 A2 * 4/2000 ............ C12Q/1/68

OTHER PUBLICATIONS

Van Veldhuizen, PJ, et al, p53 expression in incidental prostatic cancer, American Journal of Medical Sciences, vol. 305, pp. 275–279 (abstract only).*

Nagase, T, et al, Prediction of the coding sequences of unidentified human genes. III. The coding sequences of 40 new genes (KIAA0081–KIAA0120) deduced by analysis of cDNA clones from human cell line KG–1, DNA Research, vol. 2, pp. 37–43.*

Kadkol, SS, p53 and c–erB–2 expression in human prostatic adenocarcinoma cell lines and tumor tissues, Diss. Abstr. Int. [B], vol. 56, p. 2571.*

Yu, P, et al, 2001, p15PAF, a novel PCNA associated factor with increased expression in tumor tissues, Oncogene, vol. 20, No. 4, pp. 484–489.*

Notterman, DA, et al, 2001, Transcriptional gene expression profiles of colorectal adenoma, adenocarcinoma, and normal tissue examined by oligonucleotide arrays, Cancer Research, vol. 61, No. 7, pp. 3124–3130.*

Chen et al., Androgen–dependent and –independent Human Prostate Xenograft Tumors as Models for Drug Activity Evaluation, Cancer Research, 58(13):2777–2783, (Jul. 1, 1998).

Nagase et al., Prediction of the Coding Sequences of Unidentified Human Genes, DNA Research 2:37–43, (1995).

Nomura et al., PubMed Accession No. D14657, Jul. 10, 1997.

Wainstein et al., CWR22: Androgen–dependent Xenograft Model Derived from a Primary Human Prostatic Carcinoma, Cancer Research, 54(23):6049–6052, (Dec. 1, 1994).

* cited by examiner

*Primary Examiner*—Anthony C. Caputa
*Assistant Examiner*—Stephen L. Rawlings
(74) *Attorney, Agent, or Firm*—Fish & Richardson, PC

(57) ABSTRACT

The invention concerns the use of KIAA0101 nucleic acids and polypeptides in prostate cancer diagnostic and drug screening methods.

14 Claims, 1 Drawing Sheet

1 gtgaaacacc ctcggctggg aagtcagttc gttctctcct ctcctctctt cttgtttgaa
61 catggtgcgg actaaagcag acagtgttcc aggcacttac agaaaagtgg tggctgctcg
121 agcccccaga aaggtgcttg gttcttccac ctctgccact aattcgacat cagtttcatc
181 gaggaaagct gaaaataaat atgcaggagg gaaccccgtt tgcgtgcgcc caactcccaa
241 gtggcaaaaa ggaattggag aattctttag gttgtcccct aaagattctg aaaaagagaa
301 tcagattcct gaagaggcag gaagcagtgg cttaggaaaa gcaaagagaa aagcatgtcc
361 tttgcaacct gatcacacaa atgatgaaaa agaatagaac tttctcattc atctttgaat
421 aacgtctcct tgtttaccct ggtattctag aatgtaaatt tacataaatg tgtttgttcc
481 aattagcttt gttgaacagg catttaatta aaaaatttag gtttaaattt agatgttcaa
541 aagtagttgt gaaatttgag aatttgtaag actaattatg gtaacttagc ttagtattca
601 atataatgca ttgtttggtt tcttttacca aattaagtgt ctagttcttg ctaaaatcaa
661 gtcattgcat tgtgttctaa ttacaagtat gttgtatttg agatttgctt agattgttgt
721 actgctgcca ttttattgg tgtttgatta ttggaatggt gccatattgt cactccttct
781 acttgcttta aaaagcagag ttagattttt gcacattaaa aaattcagta ttaatt

FIG. 1

MVRTKADSVPGTYRKVVAARAPRKVLGSSTSATNSTSVSSRKAENKYAGGNPVCVRPTPKWQKGIGEFFRLSPKD
SEKENQIPEEAGSSGLGKAKRKACPLQPDHTNDEKE

FIG. 2 atggtgcgg actaaagcag acagtgttcc aggcacttac agaaaagtgg tggctgctcg
agcccccaga aaggtgcttg gttcttccac ctctgccact aattcgacat cagtttcatc
gaggaaagct gaaaataaat atgcaggagg gaaccccgtt tgcgtgcgcc caactcccaa
gtggcaaaaa ggaattggag aattctttag gttgtcccct aaagattctg aaaaagagaa
tcagattcct gaagaggcag gaagcagtgg cttaggaaaa gcaaagagaa aagcatgtcc
tttgcaacct gatcacacaa atgatgaaaa agaa

FIG. 3

DIAGNOSTIC AND SCREENING METHODS EMPLOYING KIAA0101

RELATED APPLICATION INFORMATION

This application claims priority from provisional application serial No. 60/113,581, filed Dec. 24, 1998, which is now abandoned.

BACKGROUND OF THE INVENTION

Prostate cancer is the most commonly diagnosed cancer and the second most common cause of death from cancer in American men. Prostate cancer cells often initially rely on androgen (e.g., testosterone) for their growth and maintenance. Therefore, androgen withdrawal, by castration or through the use of an anti-androgenic drug, is a common treatment for prostate cancer. In many cases, however, prostate cancer patients develop androgen-independent prostate cancer so that androgen withdrawal treatment is no longer effective.

The complex process of prostate tumor growth and development involves multiple gene products. Therefore, it is important to identify genes involved in tumor development, growth, and androgen dependence, particularly those genes and gene products that can serve as targets for the diagnosis, prevention, and treatment of prostate cancer.

SUMMARY OF THE INVENTION

The present invention concerns diagnostic, therapeutic, and screening methods employing KIAA0101 (Genbank Accession No. D14657).

KIAA0101 is expressed in an androgen-responsive prostate cancer cell line LNCaP. In the presence of casodex, an anti-androgen, expression is decreased 3-fold. In contrast, KIAA0101 is constitutively expresssed in androgen-independent prostate cancer cells.

Because androgen is required for optimal growth and survival of androgen-responsive prostate cancer cells, genes such KIAA0101 whose expression is decreased in the presence of casodex, an anti-androgen, are potential therapeutic targets. An agent which decreases the expression or activity of KIAA0101 may slow the growth of, arrest the growth of, or kill prostate cancer cells, including androgen-independent prostate cancer cells. Moreover, because KIAA0101 is constitutively expressed by androgen-independent prostate cancer cells (e.g., CWR22R cells), it can be used to identify agents that may be useful for the treatment of androgen-independent prostate cancer.

For example, an agent which reduces the expression or activity of KIAA0101 may reduce the growth of androgen-independent prostate cancer or cause an androgen-dependent cancer to become androgen-dependent so that it can be treated with standard androgen withdrawal therapy. Of course, such an agent might also be useful for the treatment of an androgen-dependent prostate cancer.

Useful therapeutic agents can be identified using androgen-dependent prostate cancer cells (e.g., CWR22 cells) or androgen-independent prostate cancer cells (e.g., CWR22R cells) which express KIAA0101. The growth of such cells in the presence and absence of a test agent is measured (in the presence or absence of an androgen). Compounds which reduce cell growth, reduce KIAA0101 expression, or reduce KIAA0101 activity are potential therapeutic agents for the treatment of prostate cancer (e.g., androgen-independent prostate cancer)

Because KIAA0101 expression in androgen-sensitive prostate cancer cells is decreased in the presence of casodex, an anti-androgen, KIAA0101 expression or activity can serve as a marker for monitoring anti-androgen therapy. For example, KIAA0101 should not be expressed at a significant level in prostate cancer cells of patients undergoing anti-androgen therapy. An increase over time in KIAA0101 expression or activity in the prostate cancer cells of a patient undergoing anti-androgen therapy indicates that the therapy is becoming less effective. Such an increase can also indicate that the cancer is androgen-independent. In this and other assays of KIAA0101 expressioon, the measured level of KIAA0101 expression is preferably normalized to the expression level of a non-regulated (e.g., housekeeping) gene such as actin.

Thus, the invention also features diagnostic methods and prognostic methods which can be used to identify patients having or at risk for developing and androgen-independent prostate cancer. KIAA0101 polypeptides and nucleic acids can be used to identify cells exhibiting or predisposed to developing prostate cancer, thereby diagnosing individuals having, or at high risk for developing, an androgen-independent prostate cancer.

The above-described diagnostic methods permit one to predict whether a selected compound, e.g., an anti-androgenic compound, can be used to treat the prostate cancer. Importantly, this determination can be made on a patient by patient basis.

In the various methods of the invention, KIAA0101 expression can be measured at the mRNA or protein level. Alternatively, expression can be measured indirectly by measuring the activity of KIAA0101 protein.

In another aspect, the present invention provides a method for detecting the presence of KIAA0101 activity or expression in a biological sample by contacting the biological sample with an agent capable of detecting an indicator of KIAA0101 activity such that the presence of KIAA0101 activity is detected in the biological sample.

In another aspect, the invention provides a method for treating prostate cancer by modulating the expression or activity of KIAA0101, the method comprising contacting a cell with an agent that modulates (inhibits or stimulates, preferably inhibits) KIAA0101 activity or expression such that KIAA0101 activity or expression in the cell is modulated. In one embodiment, the agent is an antibody that specifically binds to KIAA0101. In another embodiment, the agent modulates expression of KIAA0101 by modulating transcription, modulating mRNA splicing, or modulating mRNA translation. In yet another embodiment, the agent is a nucleic acid molecule having a nucleotide sequence that is antisense to the coding strand of KIAA0101.

In one embodiment, the methods of the present invention are used to treat a subject having a prostate cancer characterized by aberrant KIAA0101 protein activity or expression (e.g., constitutive expression in absence of an androgen or abnormally high expression in the presence of estrogen) by administering an agent which is a KIAA0101 modulator to the subject. The modulator can be a peptide, peptidomimetic, or small molecule, e.g., an organic molecule.

The present invention also provides a diagnostic assay for identifying whether a patient has or is at risk of developing prostate cancer by detecting the presence or absence of a genetic lesion or mutation in a KIAA0101 gene characterized by at least one of: (i) aberrant modification or mutation of a gene of the invention; (ii) mis-regulation of a gene of the invention (e.g., constitutive expression in the absence of androgen); and (iii) aberrant post-translational modification of a protein encoded by a gene of the invention.

In another aspect, the invention provides a method for identifying a compound for the treatment of prostate cancer (e.g., an androgen-independent prostate cancer or an androgen-dependent prostate cancer) by identifying a compound that binds to or modulates the activity of KIAA0101 protein. In general, such methods entail measuring a biological activity of KIAA0101 in the presence and absence of a test compound and identifying those compounds which alter the measured activity of KIAA0101.

The invention also features methods for identifying a compound which modulates the expression of KIAA0101 (at the mRNA or protein level) by measuring the expression of a KIAA0101 nucleic acid or protein in the presence and absence of a compound.

The present invention provides methods for detecting the presence of the activity or expression of a polypeptide of the invention in a biological sample by contacting the biological sample with an agent capable of detecting an indicator of activity such that the presence of activity is detected in the biological sample.

Differential expression refers to both quantitative, as well as qualitative, differences in the expression pattern of a gene in tumor cells treated with a particular compound (e.g., casodex) and untreated tumor cells. A differentially expressed gene can be a target gene. A target gene is a differentially expressed gene involved in a disorder (e.g., prostate cancer) such that modulation of the level of target gene expression or of target gene product activity can act to prevent and/or ameliorate symptoms of the disorder (e.g., androgen-dependent or androgen-independent prostate cancer). Compounds that modulate the expression of the target gene or the activity of the target gene product can be used in the treatment or prevention of the disorder. Thus, compounds that modulate the expression of a prostate cancer target gene or the activity of the gene product of a prostate cancer target gene can be used in treatments to deter benign cells from developing into prostate cancer cells. Still further, compounds that modulate the expression of a prostate cancer target gene or the activity of the gene product of a prostate cancer target gene can be used to design a preventive intervention in pre-neoplastic cells in individuals at high risk for developing prostate cancer.

An androgen-dependent prostate cancer cell is a cell that requires androgen for continued cell division. Conversely, and androgen-independent prostate cancer cell is a cell that can continue to divide in the absence of androgen.

Other features and advantages of the invention will be apparent from the following detailed description and claims.

BRIEF DESCRIPTION OF THE DRAWINGS

FIG. 1 depicts the cDNA sequence (SEQ ID NO:1) of human KIAA0101.

FIG. 2 depicts the predicted amino acid sequence (SEQ ID NO:2) of human KIAA0101.

FIG. 3 depicts the open reading frame of human KIAA0101 (SEQ ID NO:3).

DETAILED DESCRIPTION OF THE INVENTION

KIAA0101 (Genbank Accession No. D14657; Nagase et al. (1995) DNA Res. 2:37–43) was previously identified as an open reading frame having no known function.

KIAA0101 nucleic acids and polypeptides can be used for the treatment of prostate cancer, the monitoring of prostate cancer treatments, and the identification of prostate cancer therapeutic compounds.

Expression of KIAA0101 in LNCaP cells, a prostate cancer cell line, is 3-fold lower in the presence of casodex, an anti-androgen, than in the presence of R1881, an androgen agonist. In addition, KIAA0101 is constitutively expressed in CWR22R cells, an androgen-independent prostate cancer cell line.

Various aspects of the invention are described in further detail in the following subsections

I. Isolated Nucleic Acid Molecules

Describe below are various methods for making and using KIAA0101 nucleic acid molecules. These methods are useful in carrying out the methods of the invention. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA. An "isolated" nucleic acid molecule is one which is separated from other nucleic acid molecules which are present in the natural source of the nucleic acid molecule. Preferably, an "isolated" nucleic acid molecule is free of sequences (preferably protein encoding sequences) which naturally flank the nucleic acid (i.e., sequences located at the 5' and 3' ends of the nucleic acid) in the genomic DNA of the organism from which the nucleic acid is derived. An "isolated" nucleic acid molecule, such as a cDNA molecule, can be substantially free of other cellular material, or culture medium when produced by recombinant techniques, or substantially free of chemical precursors or other chemicals when chemically synthesized.

KIAA0101 nucleic acid molecules, e.g., a nucleic acid molecule having the nucleotide sequence of SEQ ID NO:1 or 3, can be isolated using standard molecular biology techniques and the sequence information provided herein. Using all or a portion of the nucleic acid sequence of SEQ ID NO:1 or 3 as a hybridization probe, nucleic acid molecules of the invention can be isolated using standard hybridization and cloning techniques (e.g., as described in Sambrook et al., eds., Molecular Cloning: A Laboratory Manual, 2nd ed., Cold Spring Harbor Laboratory, Cold Spring Harbor Laboratory Press, Cold Spring Harbor, N.Y., 1989).

A nucleic acid molecule can be amplified using cDNA, mRNA or genomic DNA as a template and appropriate oligonucleotide primers according to standard PCR amplification techniques. The nucleic acid so amplified can be cloned into an appropriate vector and characterized by DNA sequence analysis. Furthermore, oligonucleotides corresponding to all or a portion of a nucleic acid molecule of the invention can be prepared by standard synthetic techniques, e.g., using an automated DNA synthesizer.

A KIAA0101 nucleic acid molecule can comprise only a portion of a nucleic acid sequence encoding a full length polypeptide of the invention for example, a fragment which can be used as a probe or primer or a fragment encoding a biologically active portion of a polypeptide of the invention. The nucleotide sequence determined from the cloning one gene allows for the generation of probes and primers designed for use in identifying and/or cloning homologues in other cell types, e.g., from other tissues, as well as homologues from other mammals. The probe/primer typically comprises substantially purified oligonucleotide. The oligonucleotide typically comprises a region of nucleotide sequence that hybridizes under stringent conditions to at least about 12, preferably about 25, more preferably about 50, 75, 100, 125, 150, 175, 200, 250, 300, 350 or 400 consecutive nucleotides of the sense or anti-sense strand of SEQ ID NO:1 or 3.

Probes based on the sequence of KIAA0101 can be used to detect transcripts or genomic sequences encoding the same protein molecule encoded by a selected nucleic acid molecule. The probe comprises a label group attached thereto, e.g., a radioisotope, a fluorescent compound, an enzyme, or an enzyme co-factor. Such probes can be used as part of a diagnostic test kit for identifying cells or tissues which mis-express the protein, such as by measuring levels of a nucleic acid molecule encoding the protein in a sample of cells from a subject, e.g., detecting mRNA levels or determining whether a gene encoding the protein has been mutated or deleted.

A nucleic acid fragment encoding a Abiologically active portion@ of a polypeptide of the invention can be prepared by isolating or preparing a nucleic acid molecule having the sequence of a portion of SEQ ID NO:3 which encodes a polypeptide having a biological activity, expressing the encoded portion of the polypeptide protein (e.g., by recombinant expression in vitro) and assessing the activity of the encoded portion of the polypeptide.

In addition to the nucleotide sequences shown in SEQ ID NO:3, it will be appreciated by those skilled in the art that DNA sequence polymorphisms that lead to changes in the amino acid sequence may exist within a population (e.g., the human population). Such genetic polymorphisms may exist among individuals within a population due to natural allelic variation. An allele is one of a group of genes which occur alternatively at a given genetic locus. As used herein, the phrase Aallelic variant@ refers to a nucleotide sequence which occurs at a given locus or to a polypeptide encoded by the nucleotide sequence. As used herein, the terms “gene” and “recombinant gene” refer to nucleic acid molecules comprising an open reading frame encoding a polypeptide of the invention. Such natural allelic variations can typically result in 1–5% variance in the nucleotide sequence of a given gene. Alternative alleles can be identified by sequencing the gene of interest in a number of different individuals. This can be readily carried out by using hybridization probes to identify the same genetic locus in a variety of individuals.

Nucleic acid molecules corresponding to natural allelic variants and homologues of the KIAA0101 cDNA described herein can be isolated based on their identity to the nucleic acid molecule disclosed herein using a cDNA, or a portion thereof, as a hybridization probe according to standard hybridization techniques under stringent hybridization conditions.

As used herein, the term “hybridizes under stringent conditions” is intended to describe conditions for hybridization and washing under which nucleotide sequences at least 60% (65%, 70%, preferably 75%) identical to each other typically remain hybridized to each other. Such stringent conditions are known to those skilled in the art and can be found in Current Protocols in Molecular Biology, John Wiley & Sons, N.Y. (1989), 6.3.1–6.3.6. A preferred, non-limiting example of stringent hybridization conditions are hybridization in 6×sodium chloride/sodium citrate (SSC) at about 45EC, followed by one or more washes in 0.2×SSC, 0.1% SDS at 50–65EC. Preferably, an isolated nucleic acid molecule of the invention that hybridizes under stringent conditions to a nucleic acid molecule having the sequence of SEQ ID NO:1 or 3, corresponds to a naturally-occurring nucleic acid molecule. As used herein, a “naturally-occurring” nucleic acid molecule refers to an RNA or DNA molecule having a nucleotide sequence that occurs in nature (e.g., encodes a natural protein).

Changes can be introduced into the KIAA0101 gene by mutation thereby leading to changes in the amino acid sequence of the encoded protein, without altering the biological activity of the protein. For example, one can make nucleotide substitutions leading to amino acid substitutions at “non-essential” amino acid residues. A “non-essential” amino acid residue is a residue that can be altered from the wild-type sequence without altering the biological activity, whereas an “essential” amino acid residue is required for biological activity. For example, amino acid residues that are not conserved or only semi-conserved among homologues of various species may be non-essential for activity and thus would be likely targets for alteration. Alternatively, amino acid residues that are conserved among the homologues of various species (e.g., murine and human) may be essential for activity and thus would not be likely targets for alteration.

An isolated nucleic acid molecule encoding a variant protein can be created by introducing one or more nucleotide substitutions, additions or deletions into the nucleotide sequence of SEQ ID NO:3 such that one or more amino acid substitutions, additions or deletions are introduced into the encoded protein. Mutations can be introduced by standard techniques, such as site-directed mutagenesis and PCR-mediated mutagenesis. Preferably, conservative amino acid substitutions are made at one or more predicted non-essential amino acid residues. A “conservative amino acid substitution” is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Alternatively, mutations can be introduced randomly along all or part of the coding sequence, such as by saturation mutagenesis, and the resultant mutants can be screened for biological activity to identify mutants that retain activity. Following mutagenesis, the encoded protein can be expressed recombinantly and the activity of the protein can be determined.

Antisense nucleic acid molecules, i.e., molecules which are complementary to a sense nucleic acid encoding all or a part of KIAA0101 can be useful in various methods of the invention. The antisense nucleic acid can be complementary to an entire coding strand, or to only a portion thereof, e.g., all or part of the protein coding region (or open reading frame). An antisense nucleic acid molecule can be antisense to all or part of a noncoding region of the coding strand of a nucleotide sequence encoding a polypeptide of the invention. The noncoding regions (“5' and 3' untranslated regions”) are the 5' and 3' sequences which flank the coding region and are not translated into amino acids.

An antisense oligonucleotide can be, for example, about 5, 10, 15, 20, 25, 30, 35, 40, 45 or 50 nucleotides in length. An antisense nucleic acid can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject or generated in situ such that they hybridize with or bind to cellular mRNA and/or genomic DNA encoding a selected polypeptide of the invention to thereby inhibit expression, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major grove of the double helix. An example of a route of administration of antisense nucleic acid molecules of the invention includes direct injection at a tissue site. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

An antisense nucleic acid molecule of the invention can be an á-anomeric nucleic acid molecule. An á-anomeric nucleic acid molecule forms specific double-stranded hybrids with complementary RNA in which, contrary to the usual â-units, the strands run parallel to each other (Gaultier et al. (1987) Nucleic Acids Res. 15:6625–6641). The antisense nucleic acid molecule can also comprise a 2'-o-methylribonucleotide (Inoue et al. (1987) Nucleic Acids Res. 15:6131–6148) or a chimeric RNA-DNA analogue (Inoue et al. (1987) FEBS Lett. 215:327–330).

KIAA0101 nucleic acid molecules can be modified at the base moiety, sugar moiety or phosphate backbone to improve, e.g., the stability, hybridization, or solubility of the molecule. For example, the deoxyribose phosphate backbone of the nucleic acids can be modified to generate peptide nucleic acids (see Hyrup et al. (1996) Bioorganic & Medicinal Chemistry 4(1): 5–23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup et al. (1996), supra; Perry-O'Keefe et al. (1996) Proc. Natl. Acad. Sci. USA 93: 14670–675.

PNAs can be used in therapeutic and diagnostic applications. For example, PNAs can be used as antisense or antigene agents for sequence-specific modulation of gene expression by, e.g., inducing transcription or translation arrest or inhibiting replication. PNAs can also be used, e.g., in the analysis of single base pair mutations in a gene by, e.g., PNA directed PCR clamping; as artificial restriction enzymes when used in combination with other enzymes, e.g., S1 nucleases (Hyrup (1996), supra; or as probes or primers for DNA sequence and hybridization (Hyrup (1996), supra; Perry-O'Keefe et al. (1996) Proc. Natl. Acad. Sci. USA 93: 14670–675).

In another embodiment, PNAs can be modified, e.g., to enhance their stability or cellular uptake, by attaching lipophilic or other helper groups to PNA, by the formation of PNA-DNA chimeras, or by the use of liposomes or other techniques of drug delivery known in the art. For example, PNA-DNA chimeras can be generated which may combine the advantageous properties of PNA and DNA. Such chimeras allow DNA recognition enzymes, e.g., RNAse H and DNA polymerases, to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup (1996), supra). The synthesis of PNA-DNA chimeras can be performed as described in Hyrup (1996), supra, and Finn et al. (1996) Nucleic Acids Res. 24(17):3357–63. For example, a DNA chain can be synthesized on a solid support using standard phosphoramidite coupling chemistry and modified nucleoside analogs. Compounds such as 5'-(4-methoxytrityl)amino-5'-deoxy-thymidine phosphoramidite can be used as a link between the PNA and the 5' end of DNA (Mag et al. (1989) Nucleic Acids Res. 17:5973–88). PNA monomers are then coupled in a stepwise manner to produce a chimeric molecule with a 5' PNA segment and a 3' DNA segment (Finn et al. (1996) Nucleic Acids Res. 24(17):3357–63). Alternatively, chimeric molecules can be synthesized with a 5' DNA segment and a 3' PNA segment (Peterser et al. (1975) Bioorganic Med. Chem. Lett. 5:1119–11124).

An oligonucleotide may include other appended groups such as peptides (e.g., for targeting host cell receptors in vivo), or agents facilitating transport across the cell membrane (see, e g., Letsinger et al. (1989) Proc. Natl. Acad. Sci. USA 86:6553–6556; Lemaitre et al. (1987) Proc. Natl. Acad. Sci. USA 84:648–652; PCT Publication No. WO 88/09810) or the blood-brain barrier (see, e.g., PCT Publication No. WO 89/10134). In addition, oligonucleotides can be modified with hybridization-triggered cleavage agents (see, e.g., Krol et al. (1988) Bio/Techniques 6:958–976) or intercalating agents (see, e.g., Zon (1988) Pharm. Res. 5:539–549). To this end, the oligonucleotide may be conjugated to another molecule, e.g., a peptide, hybridization triggered cross-linking agent, transport agent, hybridization-triggered cleavage agent, etc.

II. Isolated Proteins and Antibodies

KIAA0101 proteins and polypeptides are useful in the methods of the invention. These proteins and polypeptides can be isolated from cells or tissue sources by an appropriate purification scheme using standard protein purification techniques, produced by recombinant DNA techniques, or synthesized chemically using standard peptide synthesis techniques.

An "isolated" or "purified" protein or biologically active portion thereof is substantially free of cellular material or other contaminating proteins from the cell or tissue source from which the protein is derived, or substantially free of chemical precursors or other chemicals when chemically synthesized. The language "substantially free of cellular material" includes preparations of protein in which the protein is separated from cellular components of the cells from which it is isolated or recombinantly produced. Thus, protein that is substantially free of cellular material includes preparations of protein having less than about 30%, 20%, 10%, or 5% (by dry weight) of heterologous protein (also referred to herein as a "contaminating protein"). When the protein or biologically active portion thereof is recombinantly produced, it is also preferably substantially free of culture medium, i.e., culture medium represents less than about 20%, 10%, or 5% of the volume of the protein preparation. When the protein is produced by chemical synthesis, it is preferably substantially free of chemical precursors or other chemicals, i.e., it is separated from chemical precursors or other chemicals which are involved in the synthesis of the protein. Accordingly such preparations of the protein have less than about 30%, 20%, 10%, 5% (by dry weight) of chemical precursors or compounds other than the polypeptide of interest.

Biologically active KIAA0101 polypeptides may comprise amino acid sequences sufficiently identical to or derived from the amino acid sequence of the protein (e.g., the amino acid sequence of SEQ ID NO:2), which include fewer amino acids than the full length protein, and exhibit at least one activity of the corresponding full-length protein. Typically, biologically active portions comprise a domain or motif with at least one activity of the corresponding protein. A biologically active portion of a protein of the invention can be a polypeptide which is, for example, 10, 25, 50, 100 or more amino acids in length. Moreover, other biologically active portions, in which other regions of the protein are deleted, can be prepared by recombinant techniques and evaluated for one or more of the functional activities of the native form of a polypeptide of the invention.

Useful polypeptides include those having the amino acid sequence of SEQ ID NO:2. Other useful proteins are substantially identical (e.g., at least about 45%, preferably 55%, 65%, 75%, 85%, 95%, or 99%) to SEQ ID NO:2 and retain the functional activity of the protein of the corresponding naturally-occurring protein yet differ in amino acid sequence due to natural allelic variation or mutagenesis.

To determine the percent identity of two amino acid sequences or of two nucleic acids, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=# of identical positions/total # of positions (e.g., overlapping positions)×100). Preferably, the two sequences are the same length.

The determination of percent homology between two sequences can be accomplished using a mathematical algorithm. A preferred, non-limiting example of a mathematical algorithm utilized for the comparison of two sequences is the algorithm of Karlin and Altschul (1990) Proc. Natl. Acad. Sci. USA 87:2264–2268, modified as in Karlin and Altschul (1993) Proc. Natl. Acad. Sci. USA 90:5873–5877. Such an algorithm is incorporated into the NBLAST and XBLAST programs of Altschul, et al. (1990) J. Mol. Biol. 215:403–410. BLAST nucleotide searches can be performed with the NBLAST program, score=100, wordlength=12 to obtain nucleotide sequences homologous to a nucleic acid molecules of the invention. BLAST protein searches can be performed with the XBLAST program, score=50, wordlength=3 to obtain amino acid sequences homologous to a protein molecules of the invention. To obtain gapped alignments for comparison purposes, Gapped BLAST can be utilized as described in Altschul et al. (1997) Nucleic Acids Res. 25:3389–3402. Alternatively, PSI-Blast can be used to perform an iterated search which detects distant relationships between molecules. Id. When utilizing BLAST, Gapped BLAST, and PSI-Blast programs, the default parameters of the respective programs (e.g., XBLAST and NBLAST) can be used. See http://www.ncbi.nlm.nih.gov. Another preferred, non-limiting example of a mathematical algorithm utilized for the comparison of sequences is the algorithm of Myers and Miller, (1988) CABIOS 4:11–17. Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

The percent identity between two sequences can be determined using techniques similar to those described above, with or without allowing gaps. In calculating percent identity, only exact matches are counted.

Chimeric or fusion proteins are also useful in the methods of the invention. As used herein, a "chimeric protein" or "fusion protein" comprises all or part (preferably biologically active) of a polypeptide of the invention operably linked to a heterologous polypeptide (i.e., a polypeptide other than the same polypeptide of the invention). Within the fusion protein, the term "operably linked" is intended to indicate that the polypeptide of the invention and the heterologous polypeptide are fused in-frame to each other. The heterologous polypeptide can be fused to the N-terminus or C-terminus of the polypeptide of the invention.

One useful fusion protein is a GST fusion protein in which the polypeptide of the invention is fused to the C-terminus of GST sequences. Another useful fusion proteins contains a heterologous signal sequence at its N-terminus. For example, the native signal sequence of a polypeptide of the invention can be removed and replaced with a signal sequence from another protein. For example, the gp67 secretory sequence of the baculovirus envelope protein can be used as a heterologous signal sequence (Current Protocols in Molecular Biology, Ausubel et al., eds., John Wiley & Sons, 1992).

Immunoglobulin fusion proteins in which all or part of a KIAA0101 polypeptide is fused to sequences derived from a member of the immunoglobulin protein family can be useful in the methods of the invention. The immunoglobulin fusion proteins of the invention can be incorporated into pharmaceutical compositions and administered to a subject to inhibit an interaction between a ligand (soluble or membrane-bound) and a protein on the surface of a cell (receptor), to thereby suppress signal transduction in vivo. Inhibition of ligand/receptor interaction may be useful therapeutically, both for treating proliferative and differentiative disorders and for modulating (e.g. promoting or inhibiting) cell survival. Moreover, the immunoglobulin fusion proteins of the invention can be used as immunogens to produce antibodies directed against a polypeptide of the invention in a subject, to purify ligands and in screening assays to identify molecules which inhibit the interaction of receptors with ligands.

Chimeric and fusion proteins of the invention can be produced by standard recombinant DNA techniques (see, e.g., Ausubel et al., supra). Moreover, many expression vectors are commercially available that already encode a fusion moiety (e.g., a GST polypeptide).

Variants of KIAA0101 are useful in the methods of the invention. Such variants have an altered amino acid sequence which can function as either agonists (mimetics) or as antagonists. Variants can be generated by mutagenesis, e.g., discrete point mutation or truncation. An agonist can retain substantially the same, or a subset, of the biological activities of the naturally occurring form of the protein. An antagonist of a protein can inhibit one or more of the activities of the naturally occurring form of the protein by, for example, competitively binding to a downstream or upstream member of a cellular signaling cascade which includes the protein of interest. Thus, specific biological effects can be elicited by treatment with a variant of limited function. Treatment of a subject with a variant having a subset of the biological activities of the naturally occurring form of the protein can have fewer side effects in a subject relative to treatment with the naturally occurring form of the protein.

Variants which function as either agonists (mimetics) or as antagonists can be identified by screening combinatorial libraries of mutants, e.g., truncation mutants, of the protein of the invention for agonist or antagonist activity. In one embodiment, a variegated library of variants is generated by combinatorial mutagenesis at the nucleic acid level and is encoded by a variegated gene library. A variegated library of variants can be produced by, for example, enzymatically ligating a mixture of synthetic oligonucleotides into gene sequences such that a degenerate set of potential protein sequences is expressible as individual polypeptides, or alternatively, as a set of larger fusion proteins (e.g., for phage display). There are a variety of methods which can be used to produce libraries of potential variants of the polypeptides of the invention from a degenerate oligonucleotide sequence. Methods for synthesizing degenerate oligonucleotides are known in the art (see, e.g., Narang (1983) Tetrahedron 39:3; Itakura et al. (1984) Annu. Rev. Biochem. 53:323; Itakura et al. (1984) Science 198:1056; Ike et al. (1983) Nucleic Acid Res. 11:477).

In addition, a library of coding sequence fragments can be generated by treating a double stranded PCR fragment of the coding sequence of interest with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal and internal fragments of various sizes of the protein of interest.

Several techniques are known in the art for screening gene products of combinatorial libraries made by point mutations or truncation, and for screening cDNA libraries for gene products having a selected property. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected.

Recursive ensemble mutagenesis (REM), a technique which enhances the frequency of functional mutants in the libraries, can be used in combination with the screening assays to identify variants of a protein of the invention (Arkin and Yourvan (1992) Proc. Natl. Acad. Sci. USA 89:7811–7815; Delgrave et al. (1993) Protein Engineering 6(3):327–331).

KIAA0101 polypeptides can be used as an immunogen to generate antibodies using standard techniques for polyclonal and monoclonal antibody preparation. The full-length polypeptide or protein can be used or, alternatively, the invention provides antigenic peptide fragments for use as immunogens. The antigenic peptide of a protein of the invention comprises at least 8 (preferably 10, 15, 20, or 30) amino acid residues of the amino acid sequence of SEQ ID NO:2 and encompasses an epitope of the protein such that an antibody raised against the peptide forms a specific immune complex with the protein.

Preferred epitopes encompassed by the antigenic peptide are regions that are located on the surface of the protein, e.g., hydrophilic regions. A hydropathy plot or similar analyses can be used to identify hydrophilic regions.

An immunogen typically is used to prepare antibodies by immunizing a suitable subject, (e.g., rabbit, goat, mouse or other mammal). An appropriate immunogenic preparation can contain, for example, recombinantly expressed chemically synthesized polypeptide. The preparation can further include an adjuvant, such as Freund's complete or incomplete adjuvant, or similar immunostimulatory agent.

The term "antibody" as used herein refers to immunoglobulin molecules and immunologically active portions of immunoglobulin molecules, i.e., molecules that contain an antigen binding site which specifically binds an antigen, such as a polypeptide of the invention. A molecule which specifically binds to a given polypeptide of the invention is a molecule which binds the polypeptide, but does not substantially bind other molecules in a sample, e.g., a biological samnle, which naturally contains the polypeptide. Examples of immunologically active portions of immunoglobulin molecules include F(ab) and $F(ab')_2$ fragments which can be generated by treating the antibody with an enzyme such as pepsin. The invention provides polyclonal and monoclonal antibodies. The term "monoclonal antibody" or "monoclonal antibody composition", as used herein, refers to a population of antibody molecules that contain only one species of an antigen binding site capable of immunoreacting with a particular epitope.

Polyclonal antibodies can be prepared as described above by immunizing a suitable subject with a polypeptide of the invention as an immunogen. The antibody titer in the immunized subject can be monitored over time by standard techniques, such as with an enzyme linked immunosorbent assay (ELISA) using immobilized polypeptide. If desired, the antibody molecules can be isolated from the mammal (e.g., from the blood) and further purified by well-known techniques, such as protein A chromatography to obtain the IgG fraction. At an appropriate time after immunization, e.g., when the specific antibody titers are highest, antibody-producing cells can be obtained from the subject and used to prepare monoclonal antibodies by standard techniques, such as the hybridoma technique originally described by Kohler and Milstein (1975) Nature 256:495–497, the human B cell hybridoma technique (Kozbor et al. (1983) Immunol. Today 4:72), the EBV-hybridoma technique (Cole et al. (1985), Monoclonal Antibodies and Cancer Therapy, Alan R. Liss, Inc., pp. 77–96) or trioma techniques. The technology for producing hybridomas is well known (see generally Current Protocols in Immunology (1994) Coligan et al. (eds.) John Wiley & Sons, Inc., New York, N.Y.). Hybridoma cells producing a monoclonal antibody of the invention are detected by screening the hybridoma culture supernatants for antibodies that bind the polypeptide of interest, e.g., using a standard ELISA assay.

Alternative to preparing monoclonal antibody-secreting hybridomas, a monoclonal antibody directed against a KIAA0101 polypeptide can be identified and isolated by screening a recombinant combinatorial immunoglobulin library (e.g., an antibody phage display library) with the polypeptide of interest. Kits for generating and screening phage display libraries are commercially available (e.g., the Pharmacia Recombinant Phage Antibody System, Catalog No. 27-9400-01; and the Stratagene SurfZAPJ Phage Display Kit, Catalog No. 240612). Additionally, examples of methods and reagents particularly amenable for use in generating and screening antibody display library can be found in, for example, U.S. Pat. No. 5,223,409; PCT Publication No. WO 92/18619; PCT Publication No. WO 91/17271; PCT Publication No. WO 92/20791; PCT Publication No. WO 92/15679; PCT Publication No. WO 93/01288; PCT Publication No. WO 92/01047; PCT Publication No. WO 92/09690; PCT Publication No. WO 90/02809; Fuchs et al. (1991) Bio/Technology 9:1370–1372; Hay et al. (1992) Hum. Antibod. Hybridomas 3:81–85; Huse et al. (1989) Science 246:1275–1281; Griffiths et al. (1993) EMBO J. 12:725–734.

Additionally, chimeric and humanized monoclonal antibodies can be produced by recombinant DNA techniques known in the art, for example using methods described in PCT Publication No. WO 87/02671; European Patent Application 184,187; European Patent Application 171,496; European Patent Application 173,494; PCT Publication No. WO 86/01533; U.S. Pat. No. 4,816,567; European Patent Application 125,023; Better et al. (1988) Science 240:1041–1043; Liu et al. (1987) Proc. Natl. Acad. Sci. USA 84:3439–3443; Liu et al. (1987) J. Immunol. 139:3521–3526; Sun et al. (1987) Proc. Natl. Acad. Sci. USA 84:214–218; Nishimura et al. (1987) Canc. Res. 47:999–1005; Wood et al. (1985) Nature 314:446–449; and Shaw et al. (1988) J. Natl. Cancer Inst. 80:1553–1559); Morrison (1985) Science 229:1202–1207; Oi et al. (1986) Bio/Techniques 4:214; U.S. Pat. No. 5,225,539; Jones et al. (1986) Nature 321:552–525; Verhoeyan et al. (1988) Science 239:1534; and Beidler et al. (1988) J. Immunol. 141:4053–4060.

Completely human antibodies are particularly desirable for therapeutic treatment of human patients. Such antibodies can be produced using transgenic mice which are incapable of expressing endogenous immunoglobulin heavy and light chains genes, but which can express human heavy and light chain genes. The transgenic mice are immunized in the normal fashion with a selected antigen, e.g., all or a portion of a KIAA0101 polypeptide. Monoclonal antibodies directed against the antigen can be obtained using conventional hybridomd technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA and IgE antibodies. For an overview of this technology for producing human antibodies, see Lonberg and Huszar (1995, Int. Rev. Immunol. 13:65–93). For a detailed discussion of this technology for producing human antibodies and human monoclonal antibodies and protocols for producing such antibodies, see, e.g., U.S. Pat. No. 5,625,126; U.S. Pat. No. 5,633,425; U.S. Pat. No. 5,569,825; U.S. Pat. No. 5,661,016; and U.S. Pat. No. 5,545,806. In addition, companies such as Abgenix, Inc. (Freemont, Calif.), can be engaged to provide human antibodies directed against a selected antigen using technology similar to that described above.

An antibody directed against a KIAA0101 can be used to detect the protein (e.g., in a cellular lysate or cell supernatant) in order to evaluate the abundance and pattern of expression of the polypeptide. The antibodies can also be used diagnostically to monitor protein levels in tissue as part of a clinical testing procedure, e.g., to, for example, determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, â-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

III. Recombinant Expression Vectors and Host Cells

Describe below are expression vecotrs and host cells which can be used to produce KIAA0101 polypeptides that are useful in the methods of the invention. A vector is a nucleic acid molecule capable of transporting another nucleic acid to which it has been linked. One type of vector is a plasmid, a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors, expression vectors, are capable of directing the expression of genes to which they are operably linked. In general, expression vectors of utility in recombinant DNA techniques are often in the form of plasmids (vectors). Other forms of expression vectors, such as viral vectors (e.g., replication defective retroviruses, adenoviruses and adeno-associated viruses), which serve equivalent functions are also useful.

Recombinant expression vectors generally include one or more regulatory sequences, selected on the basis of the host cells to be used for expression, which is operably linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel, Gene Expression Technology: Methods in Enzymology 185, Academic Press, San Diego, Calif. (1990). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein.

The recombinant expression vectors of the invention can be designed for expression of a polypeptide of the invention in prokaryotic or eukaryotic cells, e.g., bacterial cells such as *E. coli*, insect cells (using baculovirus expression vectors), yeast cells or mammalian cells. Suitable host cells are discussed further in Goeddel, supra. Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith and Johnson (1988) Gene 67:31–40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Examples of suitable inducible non-fusion *E. coli* expression vectors include pTrc (Amann et al., (1988) Gene 69:301–315) and pET 11d (Studier et al., Gene Expression Technology: Methods in Enzymology 185, Academic Press, San Diego, Calif. (1990) 60–89). One strategy to maximize recombinant protein expression in *E. coli* is to express the protein in a host bacteria with an impaired capacity to proteolytically cleave the recombinant protein (Gottesman, Gene Expression Technology: Methods in Enzymology 185, Academic Press, San Diego, Calif. (1990) 119–128). Another strategy is to alter the nucleic acid sequence of the nucleic acid to be inserted into an expression vector so that the individual codons for each amino acid are those preferentially utilized in *E. coli* (Wada et al. (1992) Nucleic Acids Res. 20:2111–2118). Such alteration of nucleic acid sequences of the invention can be carried out by standard DNA synthesis techniques.

In another embodiment, the expression vector is a yeast expression vector. Examples of vectors for expression in yeast *S. cerivisae* include pYepSec1 (Baldari et al. (1987) EMBO J. 6:229–234), pMFa (Kurjan and Herskowitz, (1982) Cell 30:933–943), pJRY88 (Schultz et al. (1987) Gene 54:113–123), pYES2 (Invitrogen Corporation, San Diego, Calif.), and pPicZ (Invitrogen Corp, San Diego, Calif.).

Alternatively, the expression vector is a baculovirus expression vector. Baculovirus vectors available for expression of proteins in cultured insect cells (e.g., Sf 9 cells) include the pAc series (Smith et al. (1983) Mol. Cell Biol. 3:2156–2165) and the pVL series (Lucklow and Summers (1989) Virology 170:31–39).

Examples of mammalian expression vectors include pCDM8 (Seed (1987) Nature 329:840) and pMT2PC (Kaufman et al. (1987) EMBO J. 6:187–195). When used in mammalian cells, the expression vector's control functions are often provided by viral regulatory elements. Certain recombinant mammalian expression vectors are capable of directing expression preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) Genes Dev. 1:268–277), lymphoid-specific promoters (Calame and Eaton (1988) Adv. Immunol. 43:235–275), in particular promoters of T cell receptors (Winoto and Baltimore (1989) EMBO J. 8:729–733) and immunoglobulins (Banerji et al. (1983) Cell 33:729–740; Queen and Baltimore (1983) Cell 33:741–748), neuron-specific promoters (e.g., the neurofilament promoter; Byrne and Ruddle (1989) Proc. Natl. Acad. Sci. USA 86:5473–5477), pancreas-specific promoters (Edlund et al. (1985) Science 230:912–916), and mammary gland-specific promoters (e.g., milk whey promoter; U.S. Pat. No. 4,873,316 and European Application Publication No. 264,166). Developmentally-regulated promoters are also encompassed, for example the murine hox promoters (Kessel and Gruss (1990) Science 249:374–379) and the á-fetoprotein promoter (Campes and Tilghman (1989) Genes Dev. 3:537–546).

A host cell for producing recombinant protein can be any prokaryotic or eukaryotic cell (e.g., *E. coli*, insect cells, yeast or mammalian cells). Vector DNA can be introduced into prokaryotic or eukaryotic cells via conventional transformation or transfection techniques. Suitable methods for transforming or transfecting host cells can be found in Sambrook, et al. (supra), and other laboratory manuals.

IV. Uses and Methods of the Invention

KIAA0101 nucler; acids, polypeptides, and antibodies can be used in a) screening assays; and b) predictive medicine (e.g., diagnostic assays, prognostic assays, monitoring clinical trials, and pharmacogenomics). KIAA0101 nucleic acid molecules can be used to express proteins (e.g., via a recombinant expression vector in a host cell in gene therapy applications), to detect mRNA (e.g., in a biological sample) or a genetic lesion, and to modulate an activity of KIAA0101. In addition, the polypeptides of the invention can be used to screen drugs or compounds which modulate activity or expression of KIAA0101 as well as to treat disorders characterized by insufficient or excessive production of KIAA0101 or production of a form of KIAA0101 which has decreased or aberrant activity compared to the wild type protein. In addition, antibodies directed against KIAA0101 can be used to detect, isolate, and modulate activity of KIAA0101.

This invention further pertains to novel agents identified by the above-described screening assays and uses thereof for treatments as described herein.

A. Screening Assays

The invention provides a method (also referred to herein as a "screening assay") for identifying modulators, i.e., candidate or test compounds or agents (e.g., peptides, peptidomimetics, small molecules or other drugs) which bind to a KIAA0101 polypeptide or have an inhibitory or stimulatory effect on, for example, expression or activity of a KIAA0101 polypeptide, particularly an inhibitory effect on expression (e.g., expression in a prostate cancer cell in the presence of androgen).

In one embodiment, the invention provides assays for screening candidate or test compounds which bind to or modulate the activity of the membrane-bound form of a KIAA0101 polypeptide or biologically active portion thereof. The test compounds of the present invention can be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer or small molecule libraries of compounds (Lam (1997) Anticancer Drug Des. 12:145).

Examples of methods for the synthesis of molecular libraries can be found in the art, for example in: DeWitt et al. (1993) Proc. Natl. Acad. Sci. USA 90:6909; Erb et al. (1994) Proc. Natl. Acad. Sci. USA 91:11422; Zuckermann et al. (1994) J. Med. Chem. 37:2678; Cho et al. (1993) Science 261:1303; Carrell et al. (1994) Angew. Chem. Int. Ed. Engl. 33:2059; Carell et al. (1994) Angew. Chem. Int. Ed. Engl. 33:2061; and Gallop et al. (1994) J. Med. Chem. 37:1233.

Libraries of compounds may be presented in solution (e.g., Houghten (1992) Bio/Techniques 13:412–421). or on beads (Lam (1991) Nature 354:82–84), chips (Fodor (1993) Nature 364:555–556), bacteria (U.S. Pat. No. 5,223,409), spores (U.S. Pat. Nos. 5,571,698; 5,403,484; and 5,223, 409), plasmids Cull et al. (1992) Proc. Natl. Acad. Sci. USA 89:1865–1869) or phage (Scott and Smith (1990) Science 249:386–390; Devlin (1990) Science 249:404–406; Cwirla et al. (1990) Proc. Natl. Acad. Sci. USA 87:6378–6382; and Felici (1991) J. Mol. Biol. 222:301–310).

In one embodiment, an assay is a cell-based assay in which a cell which expresses a membrane-bound form of a KIAA0101 polypeptide, or a biologically active portion thereof, on the cell surface is contacted with a test compound and the ability of the test compound to bind to the polypeptide determined. The cell, for example, can be a yeast cell or a cell of mammalian origin. Determining the ability of the test compound to bind to the polypeptide can be accomplished, for example, by coupling the test compound with a radioisotope or enzymatic label such that binding of the test compound to the polypeptide or biologically active portion thereof can be determined by detecting the labeled compound in a complex. For example, test compounds can be labeled with $^{125}I$, $^{35}S$, $^{14}C$, or $^{3}H$, either directly or indirectly, and the radioisotope detected by direct counting of radioemmission or by scintillation counting.

Alternatively, test compounds can be enzymatically labeled with, for example, horseradish peroxidase, alkaline phosphatase, or luciferase, and the enzymatic label detected by determination of conversion of an appropriate substrate to product. In a preferred embodiment, the assay comprises contacting a cell which expresses a membrane-bound form of a KIAA0101 polypeptide, or a biologically active portion thereof, on the cell surface with a known compound which binds the polypeptide to form an assay mixture, contacting the assay mixture with a test compound, and determining the ability of the test compound to interact with the polypeptide, wherein determining the ability of the test compound to interact with the polypeptide comprises determining the ability of the test compound to preferentially bird to the polypeptide or a biologically active portion thereof as compared to the known compound.

In another embodiment, an assay is a cell-based assay comprising contacting a cell expressing a membrane-bound form of a KIAA0101 polypeptide, or a biologically active portion thereof, on the cell surface with a test compound and determining the ability of the test compound to modulate (e.g., stimulate or inhibit) the activity of the polypeptide or biologically active portion thereof. Determining the ability of the test compound to modulate the activity of the polypeptide or a biologically active portion thereof can be accomplished, for example, by determining the ability of the polypeptide protein to bind to or interact with a target molecule.

Determining the ability of a KIAA0101 polypeptide to bind to or interact with a target molecule can be accomplished by one of the methods described above for determining direct binding. As used herein, a "target molecule" is a molecule with which a selected polypeptide (e.g., a KIAA0101 polypeptide binds or interacts with in nature, for example, a molecule on the surface of a cell which expresses the selected protein, a molecule on the surface of a second cell, a molecule in the extracellular milieu, a molecule associated with the internal surface of a cell membrane or a cytoplasmic molecule. A target molecule can be a KIAA0101 polypeptide or some other polypeptide or protein. Determining the ability of a KIAA0101 polypeptide to bind to or interact with a target molecule can be accomplished by determining the activity of the target molecule. For example, the activity of the target molecule can be determined by detecting induction of a cellular second messenger of the target (e.g., intracellular $Ca^{2+}$, diacylglycerol, IP3, etc.), detecting catalytic/enzymatic activity of the target on an appropriate substrate, detecting the induction of a reporter gene (e.g., a regulatory element that is responsive to a KIAA0101 polypeptide operably linked to a nucleic acid encoding a detectable marker, e.g. luciferase), or detecting a cellular response, for example, cellular differentiation, or cell proliferation.

In yet another embodiment, an assay of the present invention is a cell-free assay comprising contacting a KIAA0101 polypeptide or biologically active portion thereof with a test compound and determining the ability of the test compound to bind to the polypeptide or biologically active portion thereof. Binding of the test compound to the polypeptide can be determined either directly or indirectly as described above. In a preferred embodiment, the assay includes contacting the KIAA0101 polypeptide or biologically active portion thereof with a known compound which binds the polypeptide to form an assay mixture, contacting the assay mixture with a test compound, and determining the ability of the test compound to interact with the polypeptide, wherein determining the ability of the test compound to interact with the polypeptide comprises determining the ability of the test compound to preferentially bind to the polypeptide or biologically active portion thereof as compared to the known compound.

In another embodiment, an assay is a cell-free assay comprising contacting a KIAA0101 polypeptide or biologically active portion thereof with a test compound and determining the ability of the test compound to modulate (e.g., stimulate or inhibit) the activity of the polypeptide or biologically active portion thereof. Determining the ability of the test compound to modulate the activity of the polypeptide can be accomplished, for example, by determiniig the ability of the polypeptide to bind to a target molecule by one of the methods described above for determining direct binding. In an alternative embodiment, determining the ability of the test compound to modulate the activity of the polypeptide can be accomplished by determining the ability of the KIAA0101 polypeptide to further modulate the target molecule. For example, the catalytic/enzymatic activity of the target molecule on an appropriate substrate can be determined as previously described.

In yet another embodiment, the cell-free assay comprises contacting a KIAA0101 polypeptide or biologically active portion thereof with a known compound which binds the polypeptide to form an assay mixture, contacting the assay mixture with a test compound, and determining the ability of the test compound to interact with the polypeptide, wherein determining the ability of the test compound to interact with the polypeptide comprises determining the ability of the polypeptide to preferentially bind to or modulate the activity of a target molecule.

The cell-free assays of the present invention are amenable to use of both a soluble form or the membrane-bound form of a KIAA0101 polypeptide. In the case of cell-free assays comprising the membrane-bound form of the polypeptide, it may be desirable to utilize a solubilizing agent such that the membrane-bound form of the polypeptide is maintained in solution. Examples of such solubilizing agents include non-ionic detergents such as n-octylglucoside, n-dodecylglucoside, n-dodecylmaltoside, octanoyl-N-methylglucamide, decanoyl-N-methylglucamide, Triton X-100, Triton X-114, Thesit, Isotridecypoly(ethylene glycol ether)n, 3-[(3-cholamidopropyl)dimethylamminio]-1-propane sulfonate (CHAPS), 3-[(3-cholamidopropyl) dimethylamminio]-2-hydroxy-1-propane sulfonate (CHAPSO), or N-dodecyl=N,N-dimethyl-3-ammonio-1-propane sulfonate.

In more than cne embodiment of the above assay methods of the present invention, it may be desirable to immobilize either the KIAA0101 polypeptide or its target molecule to facilitate separation of complexed from uncomplexed forms of one or both of the proteins, as well as to accommodate automation of the assay. Binding of a test compound to the polypeptide, or interaction of the polypeptide with a target molecule in the presence and absence of a candidate compound, can be accomplished in any vessel suitable for containing the reactants. Examples of such vessels include microtitre plates, test tubes, and micro-centrifuge tubes. In one embodiment, a fusion protein can be provided which adds a domain that allows one or both of the proteins to be bound to a matrix. For example, glutathione-S-transferase fusion proteins or glutathione-S-transferase fusion proteins can be adsorbed onto glutathione sepharose beads (Sigma Chemical; St. Louis, Mo.) or glutathione derivatized microtitre plates, which are then combined with the test compound or the test compound and either the non-adsorbed target protein or A KIAA0101 polypeptide, and the mixture incubated under conditions conducive to complex formation (e.g., at physiological conditions for salt and pH. Following incubation, the beads or microtitre plate wells are washed to remove any inbound components and complex formation is measured either directly or indirectly, for example, as described above. Alternatively, the complexes can be dissociated from the matrix, and the level of binding or activity of the KIAA0101 polypeptide can be determined using standard techniques.

Other techniques for immobilizing proteins on matrices can also be used in the screening assays of the invention. For example, either the KIAA0101 polypeptide or its target molecule can be immobilized utilizing conjugation of biotin and streptavidin. Biotinylated KIAA0101 polypeptide or target molecules can be prepared from biotin-NHS (N-hydroxy-succinimide) using techniques well known in the art (e.g., biotinylation kit, Pierce Chemicals; Rockford, Ill.), and immobilized in the wells of streptavidin-coated 96 well plates (Pierce Chemical). Alternatively, antibodies reactive with the KIAA0101 polypeptide or target molecules but which do not interfere with binding of the KIAA0101 polypeptide to its target molecule can be derivatized to the wells of the plate, and unbound target or polypeptidede of the invention trapped in the wells by antibody conjugation. Methods for detecting such complexes, in addition to those described above for the GST-immobilized complexes, include immunodetection of complexes using antibodies reactive with the KIAA0101 polypeptide or target molecule, as well as enzyme-linked assays which rely on detecting an enzymatic activity associated with the KIAA0101 polypeptide or target molecule.

In another embodiment, modulators of expression of a KIAA0101 polypeptide are identified in a method in which a cell is contacted with a candidate compound and the expression of the selected mRNA or protein (i.e., the mRNA or protein corresponding to a polypeptide or nucleic acid of the invention) in the cell is determined. The level of expression of the selected mRNA or protein in the presence of the candidate compound is compared to the level of expression of the selected mRNA or protein in the absence of the candidate compound. The candidate compound can then be identified as a modulator of expression of the KIAA0101 polypeptide based on this comparison. For example, when expression of the selected mRNA or protein is greater (statistically significantly greater) in the presence of the candidate compound than in its absence, the candidate compound is identified as a stimulator of the selected mRNA or protein expression. Alternatively, when expression of the selected mRNA or protein is less (statistically significantly less) in the presence of the candidate compound than in its absence, the candidate compound is identified as an inhibitor of the selected mRNA or protein expression. The level of the selected mRNA or protein expression in the cells can be determined by methods described herein.

In yet another aspect of the invention, a KIAA0101 polypeptides can be used as "bait proteins" in a two-hybrid assay or three hybrid assay (see, e.g., U.S. Pat. No. 5,283,317; Zervos et al. (1993) Cell 72:223–232; Madura et al. (1993) J. Biol. Chem. 268:12046–12054; Bartel et al. (1993) Bio/Techniques 14:920–924; Iwabuchi et al. (1993) Oncogene 8:1693–1696; and PCT Publication No. WO 94/10300), to identify other proteins, which bind to or interact with the KIAA0101 polypeptide and modulate activity of the KIAA0101 polypeptide. Such binding proteins are also likely to be involved in the propagation of signals by the KIAA0101 polypeptides as, for example, upstream or downstream elements of a signaling pathway involving the KIAA0101 polypeptide.

This invention further pertains to novel agents identified by the above-described screening assays and uses thereof for treatments as described herein.

B. Predictive Medicine

The present invention also pertains to the field of predictive medicine in which diagnostic assays, prognostic assays, pharmacogenomics, and monitoring clinical trails are used for prognostic (predictive) purposes to thereby treat an individual prophylactically. Accordingly, one aspect of the present invention relates to diagnostic assays for determining expression of a polypeptide or nucleic acid of the invention and/or activity of a KIAA0101 polypeptide, in the context of a biological sample (e.g., blood, serum, cells, tissue) to thereby determine whether an individual is afflicted with a disease or disorder, or is at risk of developing a disorder, associated with aberrant expression or activity of a KIAA0101 polypeptide. The invention also provides for prognostic (or predictive) assays for determining whether an individual is at risk of developing a disorder associated with aberrant expression or activity of a KIAA0101 polypeptide. For example, mutations in a gene of the invention can be assayed in a biological sample. Such assays can be used for prognostic or predictive purpose to thereby prophylactically treat an individual prior to the onset of a disorder characterized oy or associated with aberrant expression or activity of a KIAA0101 polypeptide.

Another aspect of the invention provides methods for expression of a nucleic acid or KIAA0101 polypeptide or activity of a KIAA0101 polypeptide in an individual to thereby select appropriate therapeutic or prophylactic agents for that individual (referred to herein as "pharmacogenomics"). Pharmacogenomics allows for the selection of agents (e.g., drugs) for therapeutic or prophylactic treatment of an individual based on the genotype of the individual (e.g., the genotype of the individual examined to determine the ability of the individual to respond to a particular agent).

Yet another aspect of the invention pertains to monitoring the influence of agents (e.g., drugs or other compounds) on the expression or activity of a KIAA0101 polypeptide in clinical trials.

These and other agents are described in further detail in the following sections.

1. Diagnostic Assays

An exemplary method for detecting the presence or absence of a polypeptide or nucleic acid of the invention in a biological sample involves obtaining a biological sample from a test subject and contaccing the biological sample with a compound or an agent capable of detecting a polypeptide or nucleic acid (e.g., mRNA, genomic DNA) of the invention such that the presfnce of a polypeptide or nucleic acid of the invention is detected in the biological sample. A preferred agent for detecting mRNA or genomic DNA encoding a KIAA0101 polypeptide is a labeled nucleic acid probe capable of hybridizing to mRNA or genomic DNA encoding a KIAA0101 polypeptide. The nucleic acid probe can be, for example, a full-length cDNA, such as the nucleic acid of SEQ ID NO:1, or a portion thereof, such as an oligonucleotide of at least 15, 30, 50, 100, 250 or 500 nucleotides in length and sufficient to specifically hybridize under stringent conditions to a mRNA or genomic DNA encoding a KIAA0101 polypeptide. Other suitable probes for use in the diagnostic assays of the invention are described herein.

A preferred agent for detecting a KIAA0101 polypeptide is an antibody capable of binding to a KIAA0101 polypeptide, preferably an antibody with a detectable label. Antibodies can be polyclonal, or more preferably, monoclonal. An intact antibody, or a fragment thereof (e.g., Fab or $F(ab')_2$) can be used. The term "labeled," with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. The term "biological sample" is intended to include tissues, cells and biological fluids isolated from a subject, as well as tissues, cells and fluids present within a subject. That is, the detection method of the invention can be used to detect mRNA, protein, or genomic DNA in a biological sample in vitro as well as in vivo. For example, in vitro techniques for detection of mRNA include Northern hybridizations and in situ hybridizations. In vitro techniques for detection of a KIAA0101 polypeptide include enzyme linked immunosorbent assays (ELISAs), Western blots, immunoprecipitations and immunofluorescence. In vitro techniques for detection of genomic DNA include Southern hybridizations. Furthermore, in vivo techniques for detection of a KIAA0101 polypeptide include introducing into a subject a labeled antibody directed against the polypeptide. For example, the antibody can be labeled with a radioactive marker whose presence and location in a subject can be detected by standard imaging techniques.

In one embodiment, the biological sample contains protein molecules from the test subject. Alternatively, the biological sample can contain mRNA molecules from the test subject or genomic DNA molecules from the test subject. A preferred biological sample is a peripheral blood leukocyte sample isolated by conventional means from a subject.

In another embodiment, the methods further involve obtaining a control biological sample from a control subject, contacting the control sample with a compound or agent capable of detecting a KIAA0101 polypeptide or mRNA or genomic DNA encoding a KIAA0101 polypeptide, Fuch that the presence of the polypeptide or mRNA or genomic DNA encoding the polypeptide is detected in the biological sample, and comparing the presence of the polypeptide or mRNA or genomic DNA encoding the polypeptide in the control sample with the presence of the polypeptide or mRNA or genomic DNA encoding the polypeptide in the test sample.

The invention also encompasses kits for detecting the presence of a polypeptide or nucleic acid of the invention in a biological sample (a test sample). Such kits can be used to determine if a subject is suffering from or is at increased risk of developing a disorder associated with aberrant expression of a KIAA0101 polypeptide (e.g., androgen-independent prostate cancer). For example, the kit can comprise a labeled compound or agent capable of detecting the polypeptide or mRNA encoding the polypeptide in a biological sample and means for determining the amount of the polypeptide or mRNA in the sample (e.g., an antibody which binds the polypeptide or an oligonucleotide probe which binds to DNA or mRNA encoding the polypeptide). Kits may also include instruction for observing that the tested subject is suffering from or is at risk of developing a disorder associated with aberrant expression of the polypeptide if the amount of the polypeptide or mRNA encoding the polypeptide is above or below a normal level.

For antibody-based kits, the kit may comprise, for example: (1) a first antibody (e.g., attached to a solid support) which binds to a KIAA0101 polypeptide; and, optionally, (2) a second, different antibody which binds to either the polypeptide or the first antibody and is conjugated to a detectable agent.

For oligonucleotide-based kits, the kit may comprise, for example: (1) an oligonucleotide, e.g., a detectably labeled oligonucleotide, which hybridizes to a nucleic acid sequence encoding a KIAA0101 polypeptide or (2) a pair of primers useful for amplifying a nucleic acid molecule encoding a KIAA0101 polypeptide.

The kit may also comprise, e.g., a buffering agent, a preservative, or a protein stabilizing agent. The kit may also comprise components necessary for detecting the detectable agent (e.g., an enzyme or a substrate). The kit may also contain a control sample or a series of control samples which can be assayed and compared to the test sample contained. Each component of the kit is usually enclosed within an individual container and all of the various containers are within a single package along with instructions for observing whether the tested subject is suffering from or is at risk of developing a disorder associated with aberrant expression of the polypeptide.

2. Prognostic Assays

The methods described herein can furthermore be utilized as diagnostic or prognostic assays to identify subjects having or at risk of developing a disease or disorder associated with aberrant expression or activity of a KIAA0101 polypeptide. For example, the assays described herein, such as the preceding diagnostic assays or the following assays, can be utilized to identify a subject having or at risk of developing a disorder associated with aberrant expression or activity of a KIAA0101 polypeptide. Alternatively, the prognostic assays can be utilized to identify a subject having or at risk for developing such a disease or disorder. Thus, the present invention provides a method in which a test sample is obtained from a subject and a polypeptide or nucleic acid (e.g., mRNA, genomic DNA) of the invention is detected, wherein the presence of the polypeptide or nucleic acid is diagnostic for a subject having or at risk of developing a disease or disorder associated with aberrant expression or activity of the polypeptide. As used herein, a "test sample" refers to a biological sample obtained from a subject of interest. For example, a test sample can be a biological fluid (e.g., serum), cell sample, or tissue.

Furthermore, the prognostic assays described herein can be used to determine whether a subject can be administered an agent (e.g., an agonist, antagonist, peptidomimetic, protein, peptide,. nucleic acid, small molecule, or other drug candidate) to treat a disease or disorder associated with aberrant expression or activity of a KIAA0101 polypeptide. For example, such methods can be used to determine whether a subject can be effectively treated with a specific agent or class of agents (e.g., agents of a type which decrease activity of the polypeptide). Thus, the present invention provides methods for determining whether a subject can be effectively treated with an agent for a disorder associated with aberrant expression or activity of a KIAA0101 polypeptide in which a test sample is obtained and the polypeptide or nucleic acid encoding the polypeptide is detected (e.g., wherein the presence of the polypeptide or nucleic acid is diagnostic for a subject that can be administered the agent to treat a disorder associated with aberrant expression or activity of the polypeptide).

The methods of the invention can also be used to detect genetic lesions or mutations in a gene of the invention, thereby determining if a subject with the lesioned gene is at risk for a disorder characterized aberrant expression or activity of a KIAA0101 polypeptide. In preferred embodiments, the methods include detecting, in a sample of cells from the subject, the presence or absence of a genetic lesion or mutation characterized by at least one of an alteration affecting the integrity of a gene encoding the KIAA0101 polypeptide, or the mis-expression of the gene encoding the KIAA0101 polypeptide. For example, such genetic lesions or mutations can be detected by ascertaining the existence of at least one of: 1) a deletion of one or more nucleotides from the gene; 2) an addition of one or more nucleotides to the gene; 3) a substitution of one or more nucleotides of the gene; 4) a chromosomal rearrangement of the gene; 5) an alteration in the level of a messenger RNA transcript of the gene; 6) an aberrant modification of the gene, such as of the methylation pattern of the genomic DNA; 7) the presence of a non-wild type splicing pattern of a messenger RNA transcript of the gene; 8) a non-wild type level of a the protein encoded by the gene; 9) an allelic loss of the gene; and 10) an inappropriate post-translational modification of the protein encoded by the gene. As described herein, there are a large number of assay techniques known in the art which can be used for detecting lesions in a gene.

In certain embodiments, detection of the lesion involves the use of a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e g., Landegran et al. (1988) Science 241:1077–1080; and Nakazawa et al. (1994) Proc. Natl. Acad. Sci. USA 91:360–364), the latter of which can be particularly useful for detecting point mutations in a gene (see, e.g., Abravaya et al. (1995) Nucleic Acids Res. 23:675–682). This method can include the steps of collecting a sample of cells from a patient, isolating nucleic acid (e.g., genomic, mRNA or both) from the cells of the sample, contacting the nucleic acid sample with one or more primers which specifically hybridize to the selected gene under conditions such that hybridization and amplification of the gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self sustained sequence replication (Guatelli et al. (1990) Proc. Natl. Acad. Sci. USA 87:1874–1878), transcriptional amplification system (Kwoh, et al. (1989) Proc. Natl. Acad. Sci. USA 86:1173–1177), Q-Beta Replicase (Lizardi et al. (1988) Bio/Technology 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in a selected gene from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, e.g., U.S. Pat. No. 5,498,531) can be used to score for the presence of specific mutations by development or loss of a ribozyme cleavage site.

In other embodiments, genetic mutations can be identified by hybridizing a sample and control nucleic acids, e.g., DNA or RNA, to high density arrays containing hundreds or thousands of oligonucleotides probes (Cronin et al. (1996) Human Mutation 7:244–255; Kozal et al. (1996) Nature Medicine 2:753–759). For example, genetic mutations can be identified in two-dimensional arrays containing light-generated DNA probes as described in Cronin et al., supra. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the selected gene and detect mutations by comparing the sequence of the sample nucleic acids with the corresponding wild-type (control) sequence. Examples of sequencing reactions include those based on techniques developed by Maxim and Gilbert ((1977) Proc. Natl. Acad. Sci. USA 74:560) or Sanger ((1977) Proc. Natl. Acad. Sci. USA 74:5463). It is also contemplated that any of a variety of automated sequencing procedures can be utilized when performing the diagnostic assays ((1995) Bio/Techniques 19:448), including sequencing by mass spectrometry (see, e.g., PCT Publication No. WO 94/16101; Cohen et al. (1996) Adv. Chromatogr. 36:127–162; and Griffin et al. (1993) Appl. Biochem. Biotechnol. 38:147–159).

Other methods for detecting mutations in a selected gene include methods in which protection from cleavage agents is used to detect mismatched bases in RNA/RNA or RNA/DNA heteroduplexes (Myers et al. (1985) Science 230:1242). In general, the technique of Amismatch cleavage@ entails providing heteroduplexes formed by hybridizing (labeled) RNA or DNA containing the wild-type sequence with potentially mutant RNA or DNA obtained from a tissue sample. The double-stranded duplexes are treated with an agent which cleaves single-stranded regions of the duplex such as which will exist due to basepair mismatches between the control and sample strands. RNA/DNA duplexes can be treated with RNase to digest mismatched regions, and DNA/DNA hybrids can be treated with S1 nuclease to digest mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, e.g., Cotton et al. (1988) Proc. Natl. Acad. Sci. USA 85:4397; Saleeba et al. (1992) Methods Enzymol. 217:286–295. In a preferred embodiment, the control DNA or RNA can be labeled for detection.

In still another embodiment, the mismatch cleavage reaction employs one or more proteins that recognize mismatched base pairs in double-stranded DNA (so called ADNA mismatch repair@ enzymes) in defined systems for detecting and mapping point mutations in cDNAs obtained from samples of cells. For example, the mutY enzyme of *E. coli* cleaves A at G/A mismatches and the thymidine DNA glycosylase from HeLa cells cleaves T at G/T mismatches (Hsu et al. (1994) Carcinogenesis 15:1657–1662). According to an exemplary embodiment. a probe based on a selected sequence, e.g., a wild-type sequence, is hybridized to a cDNA or other DNA product from a test cell(s). The duplex is treated with a DNA mismatch repair enzyme, and the cleavage products, if any, can be detected from electrophoresis protocols or the like. See, e.g., U.S. Pat. No. 5,459,039.

In other embodiments, alterations in electrophoretic mobility will be used to identify mutations in genes. For example, single strand conformation polymorphism (SSCP) may be used to detect differences in electrophoretic mobility between mutant and wild type nucleic acids (Orita et al. (1989) Proc. Natl. Acad. Sci. USA 86:2766; see also Cotton (1993) Mutat. Res. 285:125–144; Hayashi (1992) Genet. Anal. Tech. Appl. 9:73–79). Single-stranded DNA fragments of sample and control nucleic acids will be denatured and allowed to renature. The secondary structure of single-stranded nucleic acids varies according to sequence, and the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) Trends Genet. 7:5).

In yet another embodiment, the movement of mutant or wild-type fragments in polyacrylamide gels containing a gradient of denaturant is assayed using denaturing gradient gel electrophoresis (DGGE) (Myers et al. (1985) Nature 313:495). When DGGE is used as the method of analysis, DNA will be modified to insure that it does not completely denature, for example by adding a 'GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) Biophys. Chem. 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions which permit hybridization only if a perfect match is found (Saiki et al. (1986) Nature 324:163); Saiki et al. (1989) Proc. Natl. Acad. Sci. USA 86:6230). Such allele specific oligonucleotides are hybridized to PCR amplified target DNA or a number of different mutations when the oligonucleotides are attached to the hybridizing membrane and hybridized with labeled target DNA.

Alternatively, allele specific amplification technology which depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989) Nucleic Acids Res. 17:2437–2448) or at the extreme 3' end of one primer where, under appropriate conditions, mismatch can prevent or reduce polymerase extension (Prossner (1993) Tibtech 11:238). In addition, it may be desirable to introduce a novel restriction site in the region of the mutation to create cleavage-based detection (Gasparini et al. (1992) Mol. Cell Probes 6:1). It is anticipated that in certain embodiments amplification may also be performed using Taq ligase for amplification (Barany (1991) Proc. Natl. Acad. Sci. USA 88:189). In such cases, ligation will occur only if there is a perfect snatch at the 3' end of the 5' sequence making it possible to detect the presence of a known mutation at a specific site by looking for the presence or absence of amplification.

The methods described herein may be performed, for example, by utilizing pre-packaged diagnostic kits comprising at least one probe nucleic acid or antibody reagent described herein, which may be conveniently used, e.g., in clinical settings to diagnose patients exhibiting symptoms or family history of a disease or illness involving a gene encoding a KIAA0101 polypeptide.

Furthermore, any cell type or tissue, preferably peripheral blood leukocytes, in which the KIAA0101 polypeptide is expressed may be utilized in the prognostic assays described herein.

3. Pharmacogenomics

Agents, or modulators which have a stimulatory or inhibitory effect on activity or expression of a KIAA0101 polypeptide as identified by a screening assay described herein can be administered to individuals to treat (prophylactically or therapeutically) disorders associated with aberrant activity of the polypeptide. In conjunction with such treatment, the pharmacogenomics (i.e., the study of the relationship between an individual's genotype and that individual's response to a foreign compound or drug) of the individual may be considered. Differences in metabolism of therapeutics can lead to severe toxicity or therapeutic failure by altering the relation between dose and blood concentration of the pharmacologically active drug. Thus, the pharmacogenomics of the individual permits the selection of effective agents (e.g., drugs) for prophylactic or therapeutic treatments based on a consideration of the individual's genotype. Such pharmacogenomics can further be used to determine appropriate dosages and therapeutic regimens. Accordingly, the activity of a KIAA0101 polypeptide, expression of a nucleic acid of the invention, or mutation content of a gene of the invention in an individual can be determined to thereby select appropriate agent(s) for therapeutic or prophylactic treatment of the individual.

Pharmacogenomics deals with clinically significant hereditary variations in the response to drugs due to altered drug disposition and abnormal action in affected persons. See, e.g., Linder (1997) Clin. Chem. 43(2):254–266. In general, two types of pharmacogenetic conditions can be differentiated. Genetic conditions transmitted as a single factor altering the way drugs act on the body are referred to as "altered drug action." Genetic conditions transmitted as single factors altering the way the body acts on drugs are referred to as "altered drug metabolism". These pharmacogenetic conditions can occur either as rare defects or as polymorphisms.

Thus, the activity of a KIAA0101 polypeptide, expression of a nucleic acid encoding the polypeptide, or mutation content of a gene encoding the polypeptide in an individual can be determined to thereby select appropriate agent(s) for therapeutic or prophylactic treatment of the individual. In addition, pharmacogenetic studies can be used to apply genotyping of polymorphic alleles encoding drug-metabolizing enzymes to the identification of an individual's drug responsiveness phenotype. This knowledge, when applied to dosing or drug selection, can avoid adverse reactions or therapeutic failure and thus enhance therapeutic or prophylactic efficiency when treating a subject with a modulator of activity or expression of the polypeptide, such as a modulator identified by one of the exemplary screening assays described herein.

4. Monitoring of Effects During Clinical Trials

Monitoring the influence of agents (e.g., drugs, compounds) on the expression or activity of a KIAA0101 polypeptide (e.g., the ability to modulate aberrant cell proliferation and/or differentiation) can be applied not only in basic drug screening, but also in clinical trials. For example, the effectiveness of an agent, as determined by a screening assay as described herein, to increase gene expression, protein levels or protein activity, can be monitored in clinical trials of subjects exhibiting decreased gene expression, protein levels, or protein activity. Alternatively, the effectiveness of an agent, as determined by a screening assay, to decrease gene expression, protein levels or protein activity, can be monitored in clinical trials of subjects exhibiting increased gene expression, protein levels, or protein activity. In such clinical trials, expression or activity of a KIAA0101 polypeptide and preferably, that of other polypeptides that have been implicated in prostate cancer, can be used as a markers.

For example, and not by way of limitation, genes, including those of the invention, that are modulated in cells by treatment with an agent (e.g., compound, drug or small molecule) which modulates activity or expression of a KIAA0101 polypeptide (e.g., as identified in a screening assay described herein) can be identified. Thus, to study the effect of agents on prostate cancer, e.g., androgen-independent prostate cancer, for example, in a clinical trial, cells can be isolated and RNA prepared and analyzed for the levels of expression of a gene of the invention and other genes implicated in the disorder. The levels of gene expression (i.e., a gene expression pattern) can be quantified by Northern blot analysis or RT-PCR, as described herein, or alternatively by measuring the amount of protein produced, by one of the methods as described herein, or by measuring the levels of activity of a gene of the invention or other genes. In this way, the gene expression pattern can serve as a marker, indicative of the physiological response of the cells to the agent. Accordingly, this response state may be determined before, and at various points during, treatment of the individual with the agent.

In a preferred embodiment, the present invention provides a method for monitoring the effectiveness of treatment of a subject with an agent (e.g., an agonist, antagonist, peptidomimetic, protein, peptide, nucleic acid, small molecule, or other drug candidate identified by the screening assays described herein) comprising the steps of (i) obtaining a pre-administration sample from a subject prior to administration of the agent; (ii) detecting the level of the polypeptide or nucleic acid of the invention in the pre-administration sample (optionally, in the presence and absence of an androgen); (iii) obtaining one or more post-administration samples from the subject; (iv) detecting the level the of the polypeptide or nucleic acid of the invention in the post-administration samples (optionally, in the presence and absence of an androgen); (v) comparing the level (or androgen inducibility) of the polypeptide or nucleic acid of the invention in the pre-administration sample with the level of the polypeptide or nucleic acid of the invention in the post-administration sample or samples; and (vi) altering the administration of the agent to the subject accordingly. For example, increased administration of the agent may be desirable to reduce expression or activity of the polypeptide, i.e., to increase the effectiveness of the agent.

EXAMPLES

Example 1

Identification of a Human cDNA Encoding KIAA0101

Human KIAA0101 cDNA was identified using a strategy designed to identify genes that are differentially expressed in casodex-treated prostate cancer cells and testosterone-treated cancer cells.

WT LNCaP cells (androgen-sensitive prostate cancer cells) were routinely grown in T162 flasks coated with Matrigel in RPMI-1640 medium supplemented with 10% FBS and 50 nM testosterone.

To identify differentially expressed genes, LNCaP cells were first incubated in the absence of androgens and then treated with either testosterone or casodex. Ten T162 flasks of LNCaP cells were pre-incubated for 24.5 hours in dye-free RPMI-1640 containing 2% charcoal stripped seruna. Following pretreatment, five T162 flasks of pretreated cells were treated with testosterone-containing medium (dye-free RPMI-1640, 2% CSS, 100 nM testosterone, 0.09% DMSO), and five T162 flasks of pretreated cells were treated with casodex-containing medium (dye-free RPMI-1640, 2% CSS, 100 ıM casodex, 0.09% DMSO). After 25 hours of incubation in testosterone-containing medium or casodex-containing medium, the cells were detached from the flasks with trypsin and pelleted Total RNA was prepared from the cell pellets using the RNeasy protocol (Qiagen). Approximately 260 ıg of total RNA was obtained from each cell pellet. Next, polyA+RNA was prepared form approximately 240 ıg of each total RNA sample using the Oligotex protocol (Qiagen), approximately 6 ıg of polyA+RNA was obtained from each 240 ıg total RNA sample, and 2 ıg of each polyA+RNA sample was used for the generation of subtraction libraries using the PCR-select protocol (Clontech; Palo Alto, Calif.).

The PCR products, representing partial cDNAs of putatively differentially expressed genes, were subcloned into pCR2.1 (InVitrogen) and transformed into INValphaF[1] cells.

The cDNA inserts from individual clones of the subtraction libraries were PCR amplified and spotted onto nylon to generated high-density arrays. The arrays were probed with first strand cDNA from: WT LNCaP cells treated with 100 nM testosterone, WT LNCaP cells treated with 100 ıM casodex, or WT LNCaP cells treated with stripped serum. Quantitative analysis of radioactive signal at each cDNA spot was performed to identify the relative differential expression of each cDNA among the above cell lines and drug treatments. The clones chosen for further analysis demonstrated higher expression levels in WT LNCaP cells treated with testosterone in WT LNCaP cells treated with casodex.

Among the clones selected for further analysis was a clone encoding KIAA0101, a previously identified open reading frame of unknown function (Genbank Accession No. D14657).

Example 2

KIAA0101

The KIAA0101 cDNA of SEQ ID NO:1 (FIG. 1) has a 333 nucleotide open reading frame (SEQ ID NO:3; FIG. 3) encoding a 111 amino acid protein (SEQ ID NO:2; FIG. 2).

Example 3

Expression of KIAA0101 in Prostate Cancer Cells

This study revealed that KIAA0101 expression in LNCaP cells decreases marginally after 24 hr of androgen withdrawal and that Casodex causes a 3-fold drop in KIAA0101 expression in LNCaP cells. In CWR22 cells (a human primary prostate xenograft cell line; Wainstein et al. (1994) Cancer Res. 54:6059–52) implanted in male nude mice, KIAA0101 expression levels decrease to almost below the level of detectability in 21 days after castration. In CWR22R cells (Chen et al. (1998) Cancer Res 58:2777–83), an androgen-independent variant of CWR22 cells, KIAA0101 appears to be constitutively expressed with respect to androgen.

Example 4

Screening for Compounds Useful for the Treatment of Prostate Cancer

Compounds potentially useful for the treatment of prostate cancer can be identified as follows. Androgen independent prostate cancer cells (e.g., CWR22R cells) are cultured under suitable conditions (e.g., in T162 flasks coated with Matrigel in RPMI-1640 medium supplemented with 10% FBS and 50 nM testosterone) in the presence and absence of a test compound and the expression of KIAA0101 is measured. A compound which reduces the expression of KIAA0101 is a potential therapeutic compound for the treatment of prostate cancer. A potential therapeutic compound identified in this manner can be further analyzed by determining its effect on the growth rate of androgen-dependent prostate cancer cells (e.g., CWR22 cells).

In order to examine the effect of casodex, an anti-androgen, on the expression of KIAA0101, LNCaP cells (androgen-sensitive prostate cancer cells) were grown to 70% confluence in RPMI-1640 (10% FBS). The cultures were then pretreated for 24 hours in dye-free RPMI-1640 containing 5% charcoal stripped serum. The cultures were then treated with either 1 nM R1881 or 100 ıM casodex in RPMI-1640 containing 5% charcoal stripped serum prior to harvesting and extraction of total mRNA for expression analysis.

Compounds potentially useful for the treatment of prostate cancer can also be identified as follows. Prostate cancer cells (e.g., WT LNCaP or CWR22 cells) are stably transfected with a vector capable of constitutively expressing KIAA0101 (e.g., a vector in which expression of KIAA0101 is under the control of the CMV IE promoter). The transfected WT LNCaP cells are cultured under suitable conditions (e.g., in T162 flasks coated with Matrigel in RPMI-1640 medium supplemented with 10% FBS and 50 nM testosterone) in the presence and absence of a test compound and the growth rate of the cells is measured. A compound which reduces the growth rate of the cells is a potential therapeutic compound for the treatment of prostate cancer. A potential therapeutic compound identified in this manner can be further analyzed by determining its effect on the growth rate of androgen-independent prostate cancer cells (e.g., CWR22R). This assay can be carried out in vitro or in vivo. For an in vivo assay CWR22 or CWR22R cells are implanted in mice.

Example 5

Screening for Compounds that Reduce the Expression of KIAA0101

Compounds potentially useful for the treatment of prostate cancer can be identified as follows. Prostate cancer cells (e.g., WT LNCaP cells) are cultured under suitable conditions (e.g., in T162 flasks coated with Matrigel in RPMI-1640 medium supplemented with 10% FBS and 50 nM testosterone) in the presence and absence of a test compound. The level of KIAA0101 expression is measured in the presence and absence of the test compound. Alterations in expression can be detected by measuring KIAA0101 mRNA using one of the methods described above, e.g., quantitative PCR, or by measuring KIAA0101 protein using one of the methods described above, e.g., Western blotting using a monoclonal anti-KIAA0101 antibody.

Equivalents

Those skilled in the art will recognize, or be able to ascertain using no more than routine experimentation, many equivalents to the specific embodiments of the invention described herein. Such equivalents are intended to be encompassed by the following claims.

What is claimed is:

1. A method for determining whether a test compound alters the expression of KIAA0101 mRNA in a prostate cancer cell that expresses a gene encoding KIAA0101 mRNA, the method comprising:

a) measuring the level of KIAA0101 mRNA present in a sample comprising the prostate cancer cells not exposed to the test compound;

b) measuring the level of KIAA0101 mRNA present in a sample comprising mRNA present in the prostate cancer cells exposed to the test compound; and c) determining that the test compound alters the expression of KIAA0101 mRNA when the level of KIAA0101 mRNA measured in step a) differs from the level of KIAA0101 mRNA measured in step b); wherein the KIAA0101 mRNA is selected from the group consisting of:

i) an mRNA comprising the complete complement of the nucleotide sequence of SEQ ID NO:3 wherein each T is replaced by a U; and ii) an mRNA encoding the amino acid sequence of SEQ ID NO:2.

2. The method of claim 1 wherein the prostate cancer cells comprise in vitro cultured cells.

3. The method of claim 1 wherein the prostate cancer cells are obtained from a patient biopsy.

4. The method of claim 3 wherein the prostate cancer cells are obtained from a prostate tumor biopsy.

5. The method of claim 1 wherein the prostate cancer cells are exposed to the test compound in vitro.

6. The method of claim 1 wherein the prostate cancer cells are exposed to the test compound in the presence of an androgen.

7. The method of claim 1 wherein the prostate cancer cells are exposed to the test compound in the presence of casodex.

8. The method of claim 1 wherein the prostate cancer cells are LNCaP cells.

9. The method of claim 1 wherein the prostate cancer cells are CWR22 cells.

10. The method of claim 1 wherein the prostate cancer cells are CWR22R cells.

11. The method of claim 1 wherein the prostate cancer cells are transfected with a nucleic acid molecule comprising a constitutively expressed gene encoding a polypeptide comprising the amino acid sequence of SEQ ID NO:2.

12. The method of claim 2 wherein the in vitro cultured prostate cancer cells are androgen dependent.

13. The method of claim 2 wherein the in vitro cultured prostate cancer cells are androgen independent.

14. The method of claim 1 further comprising isolating mRNA present in the prostate cancer cells.

* * * * *

SEQUENCE LISTING

```
<160> NUMBER OF SEQ ID NOS: 3

<210> SEQ ID NO 1
<211> LENGTH: 836
<212> TYPE: DNA
<213> ORGANISM: Homo sapiens
<220> FEATURE:
<221> NAME/KEY: CDS
<222> LOCATION: (62)...(394)

<400> SEQUENCE: 1

gtgaaacacc ctcggctggg aagtcagttc gttctctcct ctcctctctt cttgtttgaa     60

c atg gtg cgg act aaa gca gac agt gtt cca ggc act tac aga aaa gtg    109
  Met Val Arg Thr Lys Ala Asp Ser Val Pro Gly Thr Tyr Arg Lys Val
    1               5                  10                  15

gtg gct gct cga gcc ccc aga aag gtg ctt ggt tct tcc acc tct gcc      157
Val Ala Ala Arg Ala Pro Arg Lys Val Leu Gly Ser Ser Thr Ser Ala
             20                  25                  30

act aat tcg aca tca gtt tca tcg agg aaa gct gaa aat aaa tat gca      205
Thr Asn Ser Thr Ser Val Ser Ser Arg Lys Ala Glu Asn Lys Tyr Ala
         35                  40                  45

gga ggg aac ccc gtt tgc gtg cgc cca act ccc aag tgg caa aaa gga      253
Gly Gly Asn Pro Val Cys Val Arg Pro Thr Pro Lys Trp Gln Lys Gly
     50                  55                  60

att gga gaa ttc ttt agg ttg tcc cct aaa gat tct gaa aaa gag aat      301
Ile Gly Glu Phe Phe Arg Leu Ser Pro Lys Asp Ser Glu Lys Glu Asn
 65                  70                  75                  80

cag att cct gaa gag gca gga agc agt ggc tta gga aaa gca aag aga      349
Gln Ile Pro Glu Glu Ala Gly Ser Ser Gly Leu Gly Lys Ala Lys Arg
                 85                  90                  95

aaa gca tgt cct ttg caa cct gat cac aca aat gat gaa aaa gaa          394
Lys Ala Cys Pro Leu Gln Pro Asp His Thr Asn Asp Glu Lys Glu
            100                 105                 110

tagaactttc tcattcatct ttgaataacg tctccttgtt taccctggta ttctagaatg    454

taaatttaca taaatgtgtt tgttccaatt agctttgttg aacaggcatt taattaaaaa    514

atttaggttt aaatttagat gttcaaaagt agttgtgaaa tttgagaatt tgtaagacta    574

attatggtaa cttagcttag tattcaatat aatgcattgt ttggtttctt ttaccaaatt    634

aagtgtctag ttcttgctaa aatcaagtca ttgcattgtg ttctaattac aagtatgttg    694

tatttgagat ttgcttagat tgttgtactg ctgccatttt tattggtgtt tgattattgg    754

aatggtgcca tattgtcact ccttctactt gctttaaaaa gcagagttag atttttgcac    814

attaaaaaat tcagtattaa tt                                              836


<210> SEQ ID NO 2
<211> LENGTH: 111
```

-continued

```
<212> TYPE: PRT
<213> ORGANISM: Homo sapiens

<400> SEQUENCE: 2

Met Val Arg Thr Lys Ala Asp Ser Val Pro Gly Thr Tyr Arg Lys Val
  1               5                  10                  15

Val Ala Ala Arg Ala Pro Arg Lys Val Leu Gly Ser Ser Thr Ser Ala
             20                  25                  30

Thr Asn Ser Thr Ser Val Ser Ser Arg Lys Ala Glu Asn Lys Tyr Ala
         35                  40                  45

Gly Gly Asn Pro Val Cys Val Arg Pro Thr Pro Lys Trp Gln Lys Gly
     50                  55                  60

Ile Gly Glu Phe Phe Arg Leu Ser Pro Lys Asp Ser Glu Lys Glu Asn
 65                  70                  75                  80

Gln Ile Pro Glu Glu Ala Gly Ser Ser Gly Leu Gly Lys Ala Lys Arg
                 85                  90                  95

Lys Ala Cys Pro Leu Gln Pro Asp His Thr Asn Asp Glu Lys Glu
            100                 105                 110


<210> SEQ ID NO 3
<211> LENGTH: 333
<212> TYPE: DNA
<213> ORGANISM: Homo sapiens

<400> SEQUENCE: 3

atggtgcgga ctaaagcaga cagtgttcca ggcacttaca gaaaagtggt ggctgctcga      60

gcccccagaa aggtgcttgg ttcttccacc tctgccacta attcgacatc agtttcatcg     120

aggaaagctg aaaataaata tgcaggaggg aaccccgttt gcgtgcgccc aactcccaag     180

tggcaaaaag gaattggaga attctttagg ttgtccccta aagattctga aaaagagaat     240

cagattcctg aagaggcagg aagcagtggc ttaggaaaag caaagagaaa agcatgtcct     300

ttgcaacctg atcacacaaa tgatgaaaaa gaa                                  333
```